(12) United States Patent
Guidotti et al.

(10) Patent No.: US 6,835,192 B1
(45) Date of Patent: Dec. 28, 2004

(54) ABSORBENT ARTICLE WITH IMPROVED LIQUID DISPERSION

(75) Inventors: Ted Guidotti, Göteborg (SE); Roy Hansson, Mölndal (SE); Urban Widlund, Pixbo (SE); Gunnar Edwardson, Bohus Björkö (SE); Peter Blomström, Göteborg (SE); Eje Österdahl, Västra Frölunda (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/979,174
(22) PCT Filed: May 16, 2000
(86) PCT No.: PCT/SE00/00967
§ 371 (c)(1),
(2), (4) Date: Jan. 29, 2002
(87) PCT Pub. No.: WO00/76447
PCT Pub. Date: Dec. 21, 2000

(30) Foreign Application Priority Data

May 27, 1999 (SE) .............................................. 9901948

(51) Int. Cl.⁷ .............................................. A61F 13/15
(52) U.S. Cl. .................................. 604/385.101; 604/378
(58) Field of Search ................................ 604/378, 381, 604/385.08, 385.101, 382

(56) References Cited

U.S. PATENT DOCUMENTS

| | | | |
|---|---|---|---|
| 3,017,304 A | | 1/1962 | Burgeni |
| 3,860,003 A | | 1/1975 | Buell |
| 4,282,874 A | | 8/1981 | Mesek |
| 4,723,953 A | * | 2/1988 | Rosenbaum et al. ........ 604/369 |
| 5,342,332 A | * | 8/1994 | Wheeler ..................... 604/349 |
| 5,348,547 A | * | 9/1994 | Payne et al. ................ 604/378 |
| 5,624,423 A | * | 4/1997 | Anjur et al. ........... 604/385.21 |
| 5,797,895 A | * | 8/1998 | Widlund et al. ....... 604/385.24 |
| 5,846,230 A | * | 12/1998 | Osborn et al. .............. 604/378 |
| 5,961,505 A | * | 10/1999 | Coe et al. ................... 604/378 |
| 6,241,714 B1 | * | 6/2001 | Raidel et al. ............... 604/378 |
| 6,534,149 B1 | * | 3/2003 | Daley et al. ................ 428/137 |
| 6,664,438 B1 | * | 12/2003 | Guidotti ..................... 604/378 |
| 6,689,935 B2 | * | 2/2004 | Chen et al. ................. 604/378 |
| 2001/0027305 A1 | * | 10/2001 | Raidel et al. ......... 604/385.101 |
| 2002/0082575 A1 | * | 6/2002 | Dan et al. ................... 604/378 |
| 2003/0097105 A1 | * | 5/2003 | Chen et al. ................. 604/378 |

FOREIGN PATENT DOCUMENTS

| | | |
|---|---|---|
| EP | 219326 | 4/1987 |
| WO | 95/00093 | 1/1995 |
| WO | 97/47263 | 12/1997 |
| WO | 98/31318 | 7/1998 |

* cited by examiner

Primary Examiner—John J. Calvert
Assistant Examiner—Michael Bogart
(74) Attorney, Agent, or Firm—Burns, Doane, Swecker & Mathis, L.L.P.

(57) ABSTRACT

An absorbent article such as a diaper or an incontinence protector, comprising at least one liquid storage region (2, 3) with high absorption capacity and at least one wicking layer (4) which overlaps at least a substantial part of the liquid storage region and which has greater liquid dispersion ability than the storage region. The wicking layer (4) is intended to disperse liquid collected locally in the article over the liquid storage region (2, 3). The aim of the invention is to improve liquid dispersion in absorbent articles. The invention is characterized in that liquid-impermeable portions (5, 6) are arranged at separate places in the article along sections of overlapping parts of the wicking layer (4) and the liquid storage region (2, 3) in order to prevent the transfer of liquid over said parts from the wicking layer to the storage region. The liquid impermeable portions (5, 6) are placed in such a way that liquid from at least one initial accumulation place in connection with wetting of the article is first dispersed in the wicking layer (4) along said portions separated from the liquid storage region (2, 3) and thereafter is dispersed further in the liquid storage region at a distance from said accumulation place.

21 Claims, 7 Drawing Sheets

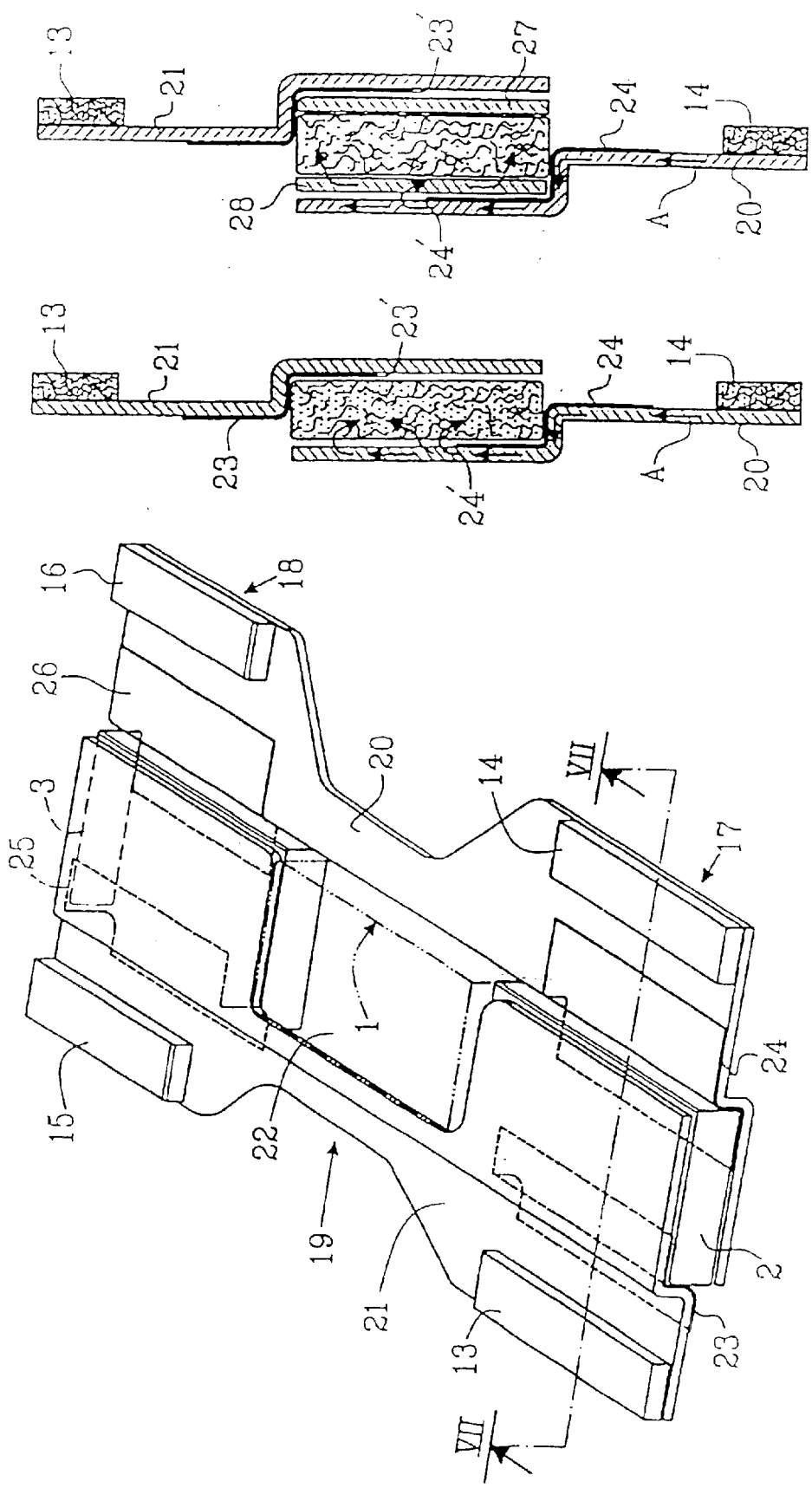

Figure 1:
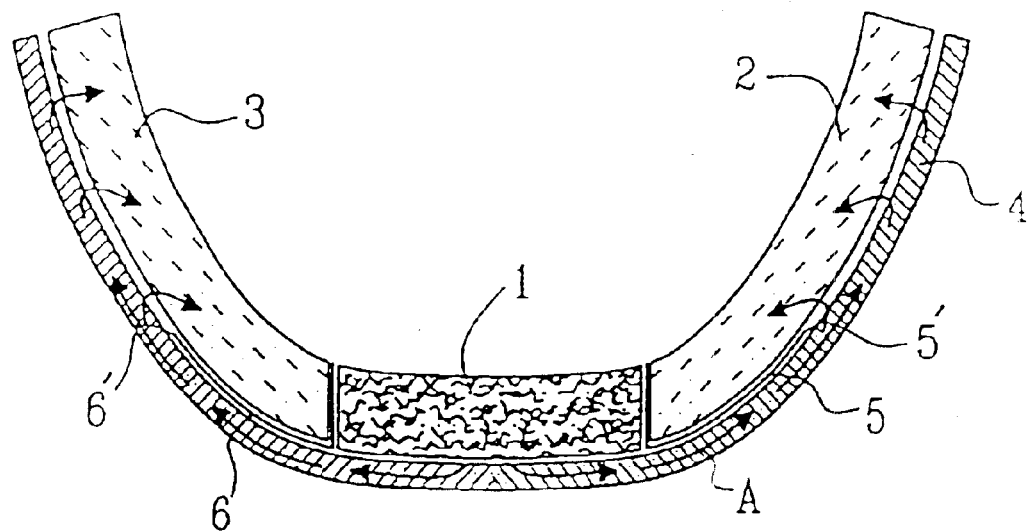

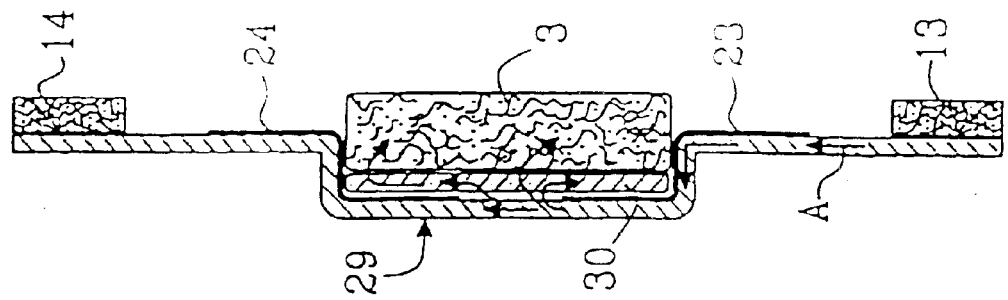
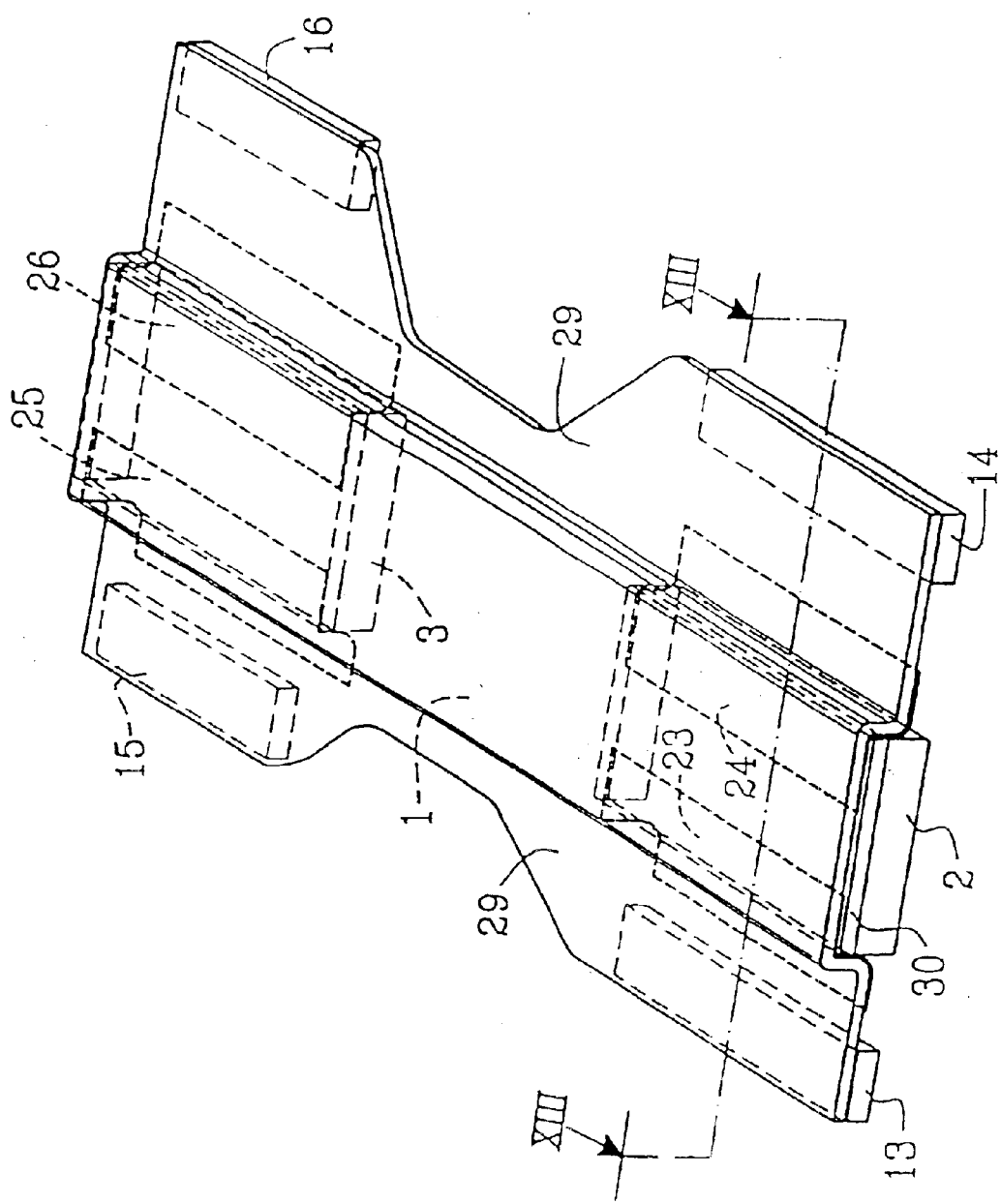

ABSORBENT ARTICLE WITH IMPROVED LIQUID DISPERSION

The present invention concerns an absorbent article, such as a diaper or an incontinence protector, comprising at least one liquid storage area with high absorption capacity and at least one wicking layer which overlaps at least a substantial part of the liquid storage area and which has greater liquid dispersion ability than the storage area, wherein the wicking layer is intended to disperse liquid collected locally in the article over the liquid storage area and wherein a liquid impermeable portion is arranged between a wicking layer and the liquid storage region.

Absorbent articles, such as diapers, pant diapers, or the like for both children and adults, are formed relatively thin in comparison with the extension in the transverse and longitudinal directions. In order to obtain sufficient capacity for accumulating emitted liquid, the absorbent material which is included in the article is spread over a large area, which area when the article is fitted on the user extends in substance from the stomach of the user via the crotch to the waist area on the back of the user.

When a user is standing or sitting, emitted urine normally ends up in the so-called 'wetting point', which is situated in the crotch portion of the diaper, and in order to avoid local leakage near the wetting point it is important that the article is formed so that liquid is spread quickly over available absorption material. As the distance to the side edges of the article is small compared with the longitudinal extension of the article, diapers, in order to decrease the risk of lateral leakage, usually have a wicking layer to spread liquid in the longitudinal direction of the article and, at the same time, measures are taken to prevent spreading in the transverse direction outside the article.

In an attempt to prevent lateral leakage, diapers are now provided with so-called leg elastic, which holds the side edges of the article in sealing contact against the body. Leg elastic of this kind is described in, for example, U.S. Pat. No. 3,860,003. In order to further improve lateral leakage security the use of upright leakage barriers on either side of the wetting point has been U.S. Pat. No. 3,860,003. In order to further improve lateral leakage security the use of upright leakage barriers on either side of the wetting point has been suggested. Leakage barriers of this type are described in, for example, EP 0 219 326 B1.

In order to spread the liquid in the longitudinal direction of the article from the wetting point, which when the user is sitting or standing is in substance the lowest point of the article, liquid must be transported upwards against the effect of gravity. This liquid dispersion problem has occupied diaper manufacturers for several decades and a number of different types of wicking layers has been suggested in order to improve dispersion in the longitudinal direction.

U.S. Pat. No. 3,017,304, which was filed as early as 1962, describes the arrangement of a wicking layer by means of wetting of one side of an absorbent body of fluff pulp and subsequent compression of the absorbent body, which compression led to the forming of a compressed wicking layer on the wetted side of the absorbent body. In modern diapers the wicking layer is usually constituted of compressed chemical fluff pulp.

Despite great efforts, no solution has as yet emerged which gives sufficient effective liquid distribution in the longitudinal direction of the diaper in order to optimally utilise available absorption material. Diapers normally leak laterally long before all absorbent material at a distance from the wetting point has been utilised. A better utilisation of absorbent material in the article is important from the point of view of economy and is also extremely desirable for environmental reasons. If absorbent material included in diapers and the like can be better utilised, the amount of necessary absorbent material in the article could be reduced, leading to a lesser need for timber raw materials and a reduction in the amount of waste which originates from used diapers mentioned above, far from optimal. However, the problems are considerably greater in other usage situations. In particular, when the user is lying down on his or her side there is a great risk of lateral leakage. Urine emitted by the user accumulates due to the force of gravity at the lower longitudinal side edge of the article and there is a great risk of a local accumulation of liquid leading to over-saturation of locally available absorbent material, which in turn can lead to direct edge leakage or to liquid running uncontrolled along the side edge and running out where gaps occur between the article and the body of the user. Thus, when the user is lying on his or her side, leakage can occur before the main part of the absorbent material in the article has been utilised.

The aim of the present invention is to improve the liquid dispersion in absorbent articles of the type mentioned in the introduction in order to obtain a better utilisation of absorbent material included in the article compared with prior art.

In accordance with the invention, this has been achieved in that liquid-impermeable portions are arranged in the article along sections of overlapping parts of the wicking layer and the liquid storage region in order to prevent the transfer of liquid over said parts from the wicking layer to the storage region, and in that said liquid impermeable portions are placed in such a way that liquid from at least one initial accumulation place, in the form of a liquid acquisition region or in the form of a liquid acquisition region and intermediate storage regions in connection with wetting of the article is first dispersed in the wicking layer along said portions separated from the liquid storage region and thereafter is dispersed further in the liquid storage region at a distance from said accumulation place.

A problem with previously known diapers or the like has been that liquid has not been able to be spread sufficiently effectively against the force of gravity with the help of wicking layers. Liquid accumulates in the lowest situated region of the article, which is constituted by the region around the wetting with the help of wicking layers. Liquid accumulates in the lowest situated region of the article, which is constituted by the region around the wetting point when the user is standing or sitting and which is constituted by the lowest situated side portions of the diaper when the user is lying down on his/her side.

In previously known constructions the wicking and storage layers are in direct communication with each other at least in mutually overlapping portions. This means that liquid is filled into the storage layers beginning from the lowest situated point and continually upwards.

This means that liquid must be lifted higher and higher against the force of gravity as liquid is emptied from the initial accumulation point. As liquid is first emptied from the initial accumulation point out of the thickest capillaries, it becomes more and more difficult to draw the liquid from the initial accumulation point. Thus, in previously known solutions two factors act together and make the dispersion to parts of the absorbent body situated at a distance more difficult. When the liquid is to be lifted highest it is most difficult to draw liquid out of the absorbent body at the initial accumulation place.

The idea of the invention in the present application is to keep the wicking layer separated from the storage region during the extent of the first dispersion from an initial accumulation place so that liquid can be lifted a distance vertically upwards only in the wicking layer before any transfer of liquid from the wicking layer to the storage layer occurs. This means that the storage layer is not filled beginning from the vertically lowest situated parts but that liquid has first been lifted up a distance in the wicking layer. By means of this design, available absorbent material in the storage layer is utilised to a considerably greater extent. The liquid begins to be dispersed in the storage layer in a higher situated point than in previously known absorbent articles and thus reaches higher situated parts of the storage layer than has previously been possible. The idea is that the lowest situated parts of the storage layer are filled last, i.e. when it is most difficult to draw liquid out of the absorbent material in the initial accumulation place.

No-one has previously suggested using liquid-impermeable layers inside absorbent bodies in order to improve liquid distribution and achieve a better utilisation of absorbent material in the article. As the more effective liquid distribution is obtained by means of the presence of a liquid-impermeable layer between parts of overlapping portions of the wicking layer and liquid storage region, the improved effect is independent of the choice of material in the wicking layer and storage region, i.e. an improvement is always obtained by means of the presence of the liquid-impermeable layer compared to when it is absent.

It has previously been suggested in U.S. Pat. No. 4,282, 874 to arrange plastic layers inside absorbent articles. However, the plastic layer in the diaper according to this publication is perforated and has the purpose of only letting liquid pass in one direction through the plastic layer, whereby the surface dryness of the article closest to the user is increased. The plastic layer in accordance with this publication covers the entire liquid storage region and therefore cannot contribute to better dispersion to portions of the liquid storage region which are situated higher during use. Furthermore, it is not arranged between the distribution layer and the storage layer, which likewise is a condition for a plastic layer arranged in an absorbent article to improve the distribution from initial accumulation places to portions situated at a distance.

WO-A-9500093 discloses an absorbent article, provided with a fluid directing component, preferably liquid impervious, which is positioned between the absorbent core and an absorbent strip, disposed immediately under the topsheet. Said absorbent strip is serving as a liquid transporting component.

No-one has previously suggested using liquid-impermeable layers inside absorbent bodies in order to improve liquid distribution and achieve a better utilisation of absorbent material in the article. As the more effective liquid distribution is obtained by means of the presence of a liquid-impermeable layer between parts of overlapping portions of the wicking layer and liquid storage region, the improved effect is independent of the choice of material in the wicking layer and storage region, i.e. an improvement is always obtained by means of the presence of the liquid-impermeable layer compared to when it is absent.

It has previously been suggested in U.S. Pat. No. 4,282, 874 to arrange plastic layers inside absorbent articles. However, the plastic layer in the diaper according to this publication is perforated and has the purpose of only letting liquid pass in one direction through the plastic layer, whereby the surface dryness of the article closest to the user is increased. The plastic layer in accordance with this publication covers the entire liquid storage region and therefore cannot contribute to better dispersion to portions of the liquid storage region which are situated higher during use. Furthermore, it is not arranged between the distribution layer and the storage layer, which likewise is a condition for a plastic layer arranged in an absorbent article to improve the distribution from initial accumulation places to portions situated at a distance.

WO-A-9500093 discloses an absorbent article, provided with a fluid directing component, preferably liquid impervious, which is positioned between the absorbent core and an absorbent strip, disposed immediately under the topsheet. Said absorbent strip is serving as a liquid transporting component.

The absorbent article in accordance with WO-A-9500093 do not work satisfactory during heavy discharges of liquid from the user as the article cannot absorb large amount of liquid quickly. The liquid will instead spread over the surface and cause side leakage.

The invention will be described in more detail below in connection with some suitable embodiment examples which are shown in the attached drawings, in which FIG. 1 shows schematically in a longitudinal section the essential parts for the present invention of an absorbent article in accordance with a first embodiment.

The absorbent article in accordance with WO-A-9500093 do not work satisfactory during heavy discharges of liquid from the user as the article cannot absorb large amount of liquid quickly. The liquid will instead spread over the surface and cause side leakage.

Figure 2:
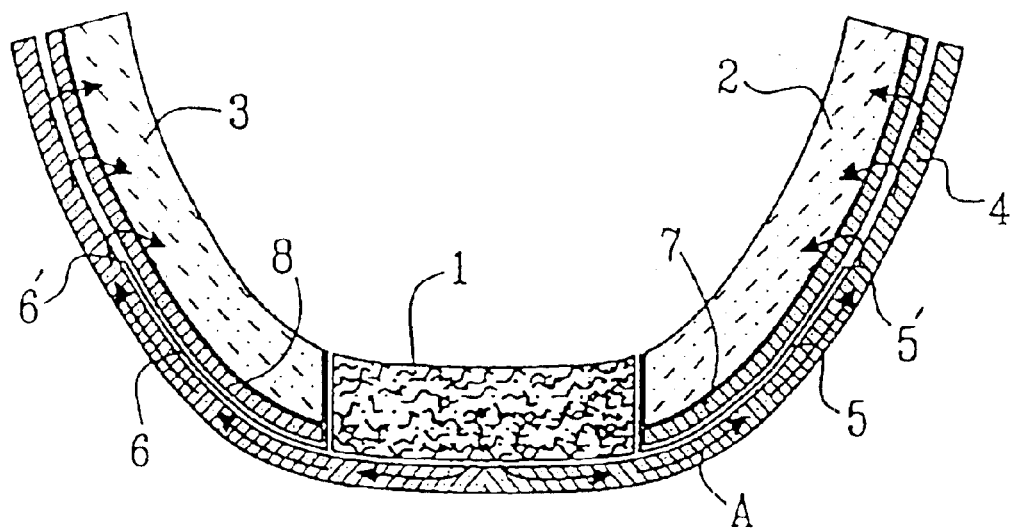
Figure 3:
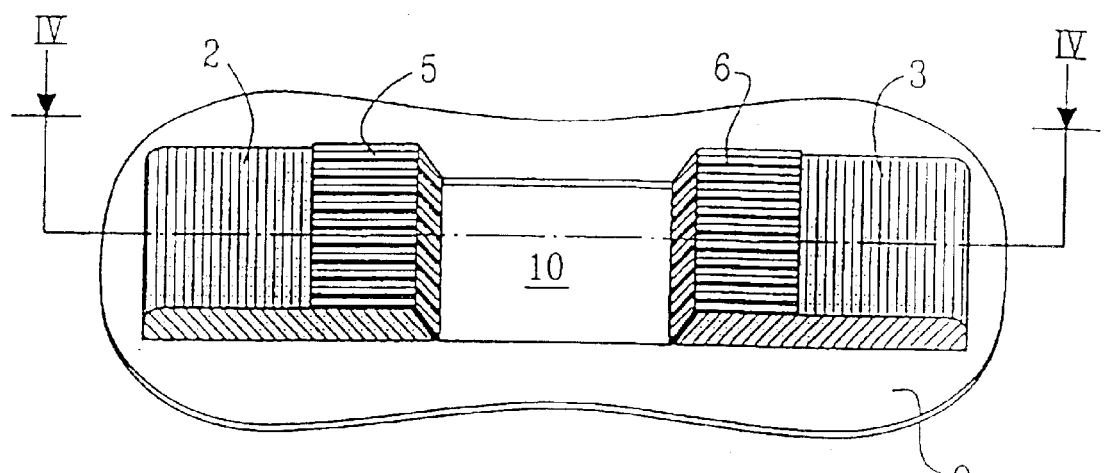
Figure 4:
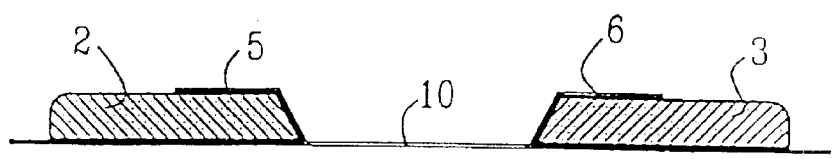
Figure 5:
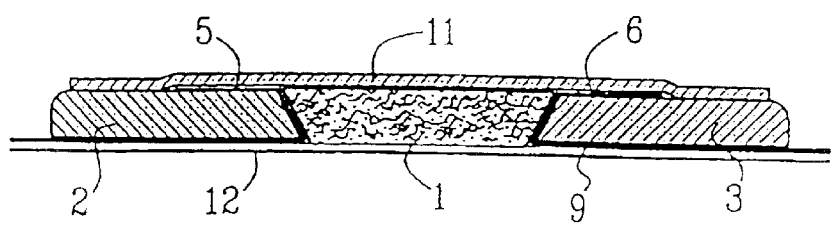
Figure 9:
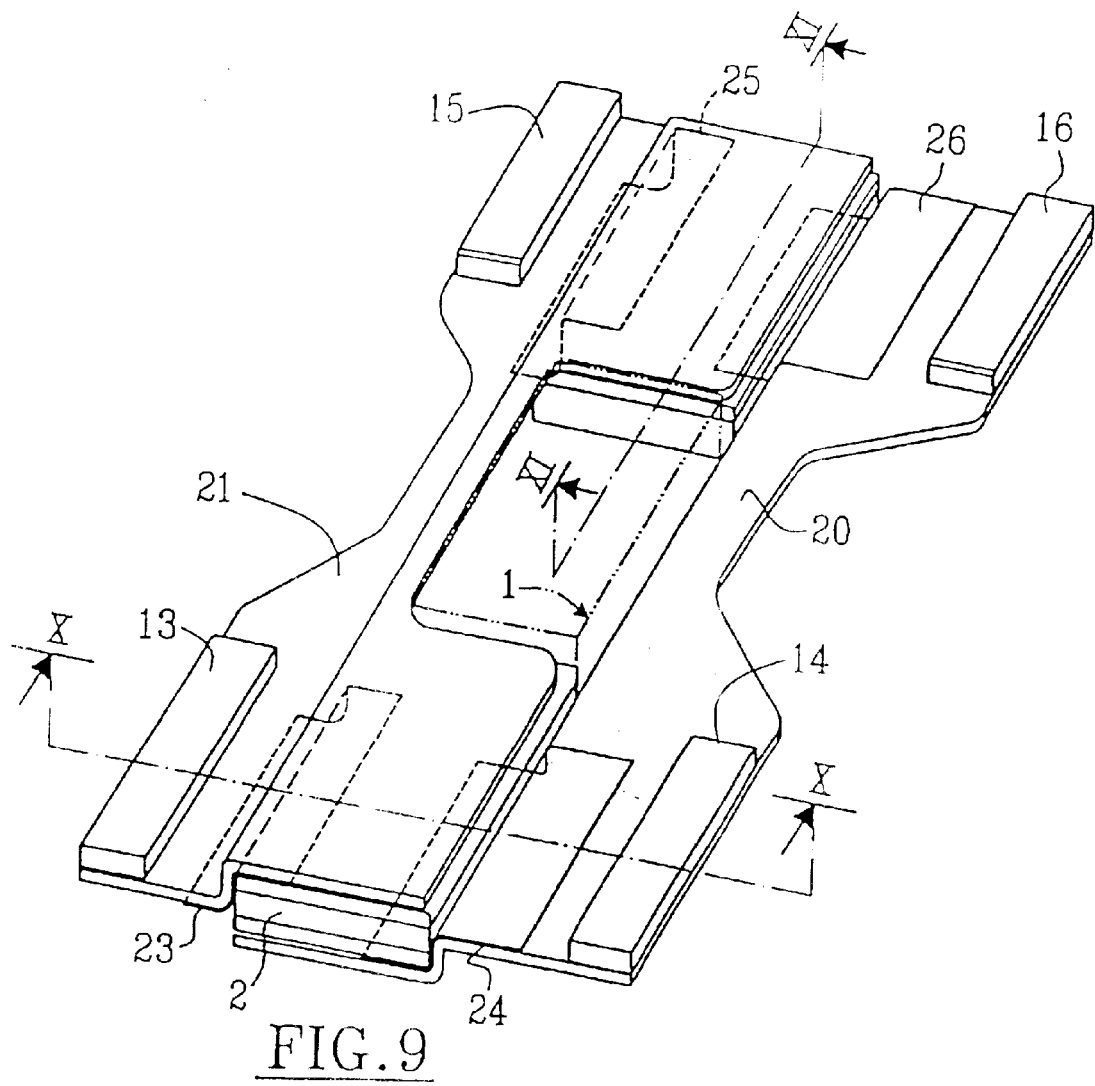
Figure 10:
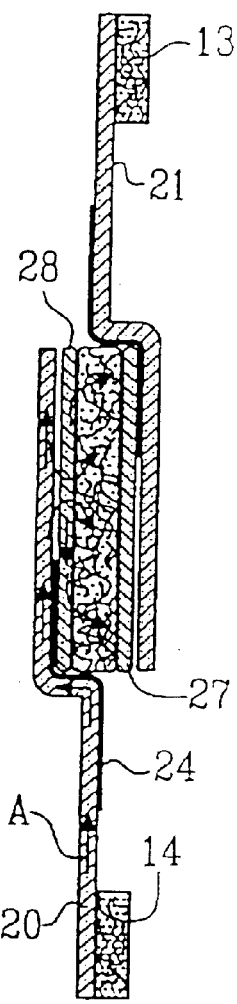
Figure 11:
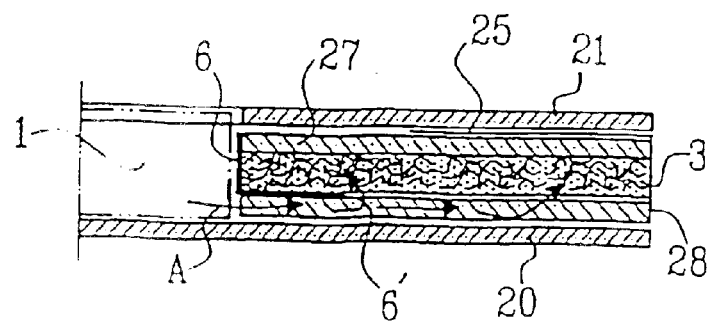
Figure 14:
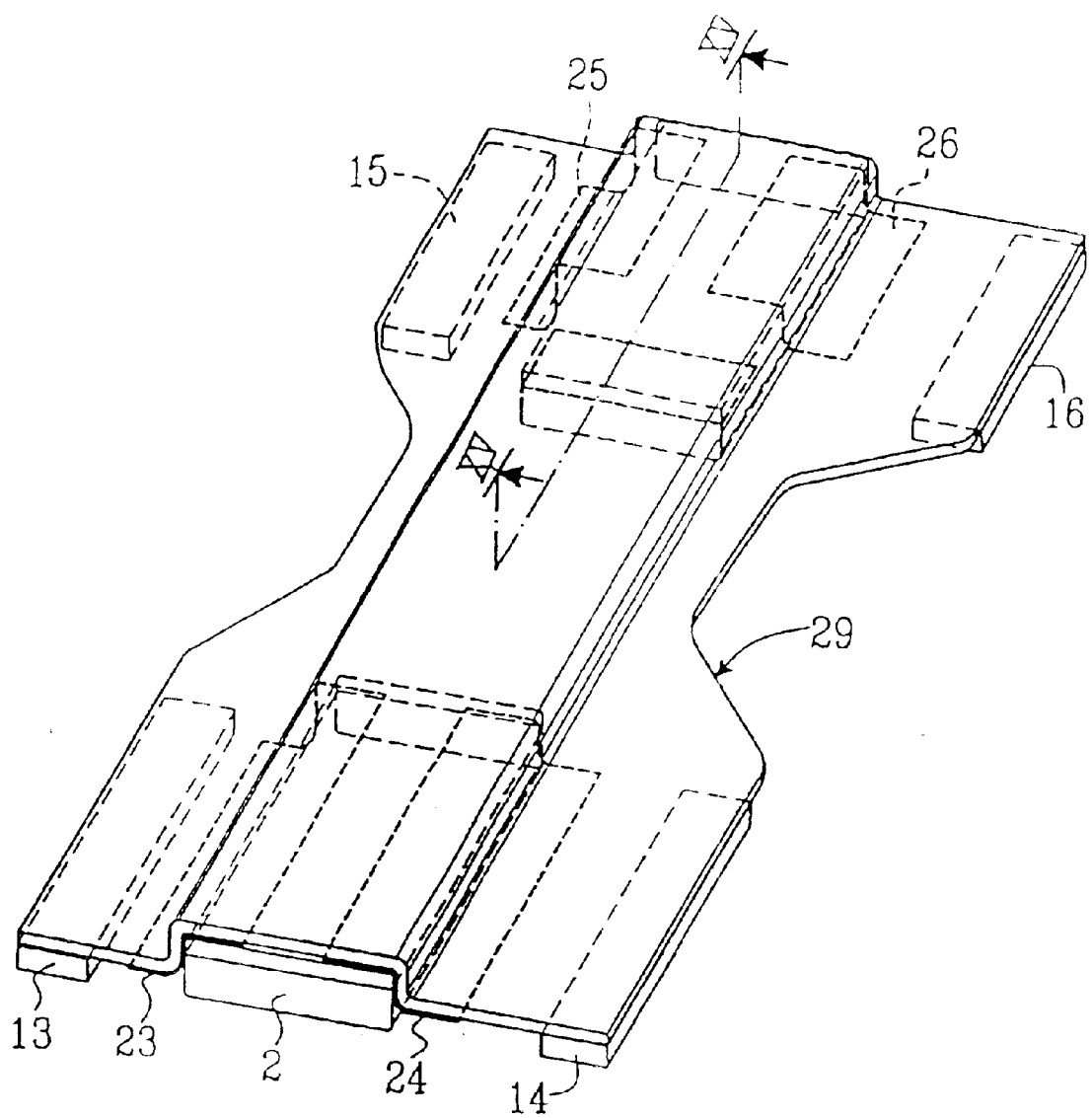
Figure 15:
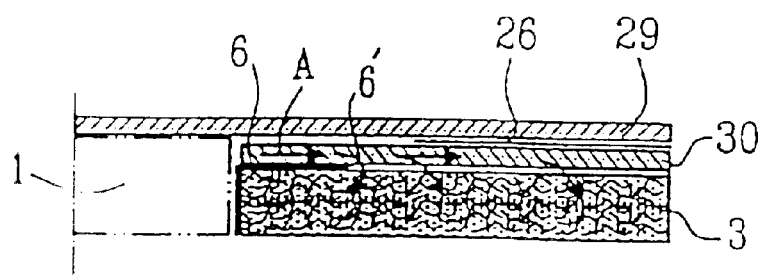

The invention will be described in more detail below in connection with some suitable embodiment examples which are shown in the attached drawings, in which FIG. 1 shows schematically in a longitudinal section the essential parts for the present invention of an absorbent article in accordance with a first embodiment, FIG. 2 shows a corresponding longitudinal section of a somewhat modified embodiment in comparison with the embodiment according to FIG. 1, FIG. 3 shows in perspective parts of an absorbent article in accordance with a third embodiment FIG. 4 shows a section along the line IV—IV in FIG. 3, FIG. 5 shows the same section as in FIG. 4 with some additional parts which are included in the third embodiment, FIG. 6 shows in perspective the essential parts of an absorbent article in accordance with a suitable fourth embodiment of the present invention, FIG. 7 shows a section along the line VII—VII in FIG. 6, FIG. 8 shows a similar section to that in FIG. 7 of a fifth embodiment which is somewhat modified in comparison with the embodiments in FIGS. 6 and 7, FIG. 9 shows in perspective the essential parts of an absorbent article in accordance with a sixth embodiment of the present invention, FIG. 10 shows a section along the line X—X in FIG. 9, FIG. 11 shows a section along the line XI—XI in FIG. 9, FIG. 12 shows in perspective the essential parts of an absorbent article in accordance with a seventh embodiment of the present invention, FIG. 13 shows a section along the line XIII—XIII in FIG. 12, FIG. 14 shows the essential parts of an absorbent article in accordance with an eighth embodiment of the present invention, FIG. 15 shows a section along the line XV—XV in FIG. 14.

The present invention can be applied in different types of absorbent articles, such as diapers for both children and adults, in so-called pant diapers and in inserts for diapers and pant diapers. As the articles in their entirety can vary in many different ways, only parts that are essential to the function of the invention are shown in the embodiment examples described below while other parts have been omitted. Details which have been omitted are, for example, enclosing covers comprising possible leg elastic and waist elastic and fastening arrangements, which can be constituted of tape, hook and loop fastenings or supporting underpants, etc.

FIG. 1 shows in a longitudinal section the absorbent parts in a diaper and in a position which these parts have when the user is standing, walking or sitting. The reference numeral 1 indicates a liquid acquisition region which is located in the crotch region of the user when the article is in use. The material in this region can be, for example, a wadding with the ability to quickly take up large amounts of liquid. The region can also be a cavity. This region 1 is located around the so-called wetting point, which refers to the 'point' of the article that is situated directly in front of the opening of the urethra of the user. Liquid storage regions 2, 3 are arranged at either end of the liquid acquisition region. A wicking layer 4 is arranged in one piece under the liquid acquisition region 1 and the two liquid storage regions 2, 3. The embodiment in accordance with FIG. 1 also includes two liquid-impermeable portions 5 and 6, which each form a liquid barrier between an end edge side of the liquid acquisition region and the end edge side of the adjacent liquid storage region 2 and 3, respectively, and also form a liquid barrier between the wicking layer and part of the respective liquid storage region nearest the liquid acquisition region. When the user is standing or sitting, the crotch area of the diaper, and thus the liquid acquisition region 1, is mainly the lowest situated area and the liquid storage regions 2 and 3 extend, as can be seen in FIG. 1, in a direction upwards from the crotch area towards the stomach of the user and towards the waist area on the back of the user, respectively. The liquid acquisition region 1 serves as an initial accumulation place for urine when the user is standing or sitting and consists of a material for example wadding, which has the ability to quickly let in liquid and which has low liquid retention ability. Arranging regions with the ability to quickly take up large amounts of liquid emitted by the user is previously known. Likewise, it is previously known to use wicking layers to empty the liquid acquisition region so that this region can once again take up liquid emitted by the user. As mentioned above, it has previously not been possible to utilise available absorbent material in the article in a completely satisfactory way. This has chiefly been due to the fact that it has not been possible to transport liquid sufficiently high up against the force of gravity from the initial accumulation place. The liquid storage regions, both in the article in accordance with the present invention and in previously known diapers or the like, are intended to be able to retain absorbed liquid and it has therefore been necessary to forgo the dispersion ability. This in itself can be compensated to a great degree by a wicking layer adjacent to the liquid storage region. As mentioned above, the problem with previously known solutions is that the liquid storage regions are filled beginning with the end located nearest the liquid acquisition region and thus the lowest parts of the diaper (when the user is standing or sitting). In this way, as the liquid acquisition region is emptied of liquid the distance vertically to non-saturated absorbent material in the liquid storage regions becomes longer and at the same time it becomes more and more difficult to draw out liquid from the liquid acquisition region. In addition, the absorption ability of the liquid storage region diminishes when this area swells during absorption.

Arranging the liquid-impermeable portions 5 and 6 prevents direct transfer of liquid from the wicking layer to the storage regions 2, 3 along the parts of the wicking layer which are covered by the liquid-impermeable portions. When a user of an absorbent article in accordance with FIG. 1 is sitting or standing, liquid is thus transported from the liquid acquisition region 1, which serves as an initial accumulation place, against the force of gravity in the direction of the arrows A along the wicking layer and separated from the liquid storage regions 2 and 3. Only when the liquid in the wicking layer has passed the end edge 5' and 6' of the liquid-impermeable layer can the liquid begin to be dispersed in the storage regions 2 and 3. The material in said storage regions can be, for example, mixtures of fluff pulp and high absorbent material, which also goes under the name of super-absorbent material and has the ability to absorb liquid equivalent to several times its own weight. The choice of material and the design of the liquid storage layers are not critical. What is essential is that the liquid storage areas have the ability to absorb large quantities of liquid and also to retain the liquid when the storage areas are under load. A common factor in all previously known absorbent bodies with high absorption capacity and high water retention ability is that the liquid dispersion in such absorbent bodies is very slow, which is compensated by separate wicking layers. Disregarding gravity, liquid spreads equally quickly in all directions in a homogeneous absorbent body. Liquid which has been transferred to the liquid storage region is thus distributed uniformly within the area, disregarding variations due to gravity.

In the embodiment example shown in FIG. 1, the wicking layer 4 overlaps the whole length of the respective storage region and liquid from the liquid acquisition region which has passed the end edges 5' and 6' can, due to the presence of the wicking layer, spread more quickly over the storage region in a direction from the crotch area than the reverse despite the force of gravity.

By means of the choice of wicking layer and the length of the liquid-impermeable portion between the storage region and an overlapping wicking layer, the absorbent article can be optimised so that those parts of the liquid storage regions that are nearest the liquid acquisition region are filled with liquid last. This is essential since the hardest bound liquid in the liquid acquisition region is emptied last and the absorbent material in the storage regions is thus best utilised if the necessary work for transporting the liquid vertically is lowest when it is most difficult to draw liquid from the liquid acquisition region. For liquid to be transported via the wicking layer from the liquid acquisition region to the liquid storage region, the suction power of the liquid storage region must exceed the liquid retention ability of the liquid acquisition region and the suction height. For liquid to be dispersed in the desired direction, the liquid affinity must be greater for the wicking layer than for the liquid acquisition region and the liquid affinity for the storage region must be higher than for the wicking layer. The liquid affinity can vary depending on capillary pressure, effective pore size, wetting angles, osmotic pressure, etc.

In the embodiment example shown in FIG. 2, the details which correspond to similar details in FIG. 1 have been given the same reference numerals. The embodiment example in FIG. 2 differs from the embodiment example in FIG. 1 in that an additional wicking layer 7 and 8, respectively, is arranged immediately behind the respective liquid storage layer 2, 3. The two liquid-impermeable portions 5 and 6 are arranged between the wicking layer 4 and the two additional wicking layers 7 and 8 and have a longer extension in the longitudinal direction of the article compared with the liquid-impermeable portions in the embodiment example in FIG. 1, i.e. the liquid barrier between the wicking layer 4 and the respective storage region is longer in the embodiment in accordance with FIG. 2. The embodiment in accordance with FIG. 2 can be suitable depending on the material included and/or whether the liquid transport distances are long. The purpose of arranging the additional wicking layer 7 and 8 is mainly that liquid that has passed the end edge 5' and 6' of the liquid-impermeable portion via the wicking layer 4 will be spread all the way down to the part of the respective storage layer that is located closest to the liquid acquisition region 1. When the liquid-impermeable portions extend over a considerable part of the storage region, there is a risk that the absorbent material in the respective storage region will not be utilised in the region closest to the liquid acquisition region. The liquid dispersion over the storage regions can, under certain circumstances, be improved by arranging an additional wicking layer 7 and 8. In the shown embodiment the additional wicking layer 7 and 8, respectively, extends over the entire liquid storage region 2 and 3, respectively. This can in itself be most suitable from the point of view of manufacturing, but an alternative is of course for the additional wicking layer to have an extension in the longitudinal direction of the liquid storage region which corresponds to the extension of the liquid-impermeable portion in this direction. The length of the liquid-impermeable portions and the design of the wicking layers are chosen for optimal utilisation of absorbent material in the storage areas dependent on the absorption and dispersion characteristics of the material in the article.

As mentioned above, arranging the liquid-impermeable portions enables a more effective utilisation of absorbent material in the article. This in turn can mean that absorbent material of poorer quality but with a much more advantageous price can be used in absorbent articles without detracting from the function. This of course also applies to the choice of liquid dispersion material.

The embodiment in accordance with FIG. 3 comprises two liquid storage regions 2 and 3. It also comprises a liquid-impermeable layer 9 which extends over the forward and rear portions of the article and which, seen from the side that is facing the user during use of the article, is arranged above said liquid storage regions 2, 3. The liquid-impermeable layer 9 has a central opening 10, which extends between the two liquid storage regions and is arranged so that it is chiefly centered around the wetting point during use of the article. The opening 10 has been formed by making slits through the liquid-impermeable layer along the longitudinal borderlines of the intended opening and a transversal slit between said lines in the centre area of the intended opening and by folding in the flaps made by the slits. As can be seen in FIGS. 3 and 4, these flaps are folded in under the liquid storage areas to form the liquid-impermeable portions 5 and 6.

FIG. 5 also shows the liquid acquisition region 1 arranged in the crotch area of the article and a wicking layer 11, which is intended to disperse liquid from the liquid acquisition region to the two liquid storage regions 2, 3. The liquid-impermeable portions 5 and 6 thereby fulfil the same function as has been described in connection with the embodiment in FIG. 1. The embodiment in FIG. 5 comprises an outer layer 12, which during use of the article is in direct contact with the skin of the user. This outer layer can consist of, for example, nonwoven. Examples of other suitable outer layers are a fibre layer consisting of long "endless" fibres which are welded together in separate points, or of a foam material. An essential characteristic of this outer layer is that it quickly allows liquid to penetrate from the outside into the absorbent article.

In the embodiment in accordance with FIGS. 3–5, a liquid-impermeable layer intended to prevent rewetting of liquid absorbed in the article to the skin of the user has been used to form the liquid-impermeable portions 5, 6, which promote dispersion of liquid over the liquid storage regions.

As has been mentioned above, the risk of leakage from diapers or the like is especially great when the user is lying down on his/her side. Due to gravity, liquid runs from the wetting point towards the lowest situated edge on the article. The vertically lowest situated parts of a diaper with a tapering crotch area are the edge portions of the diaper at each end of the crotch area, i.e. the forward and rear portions. In modern diapers at least the crotch area is sealed laterally with leg elastic and with additional upright liquid barriers. There is therefore a great risk that when the user is lying down on his/her side considerable amounts of liquid can accumulate in the lowest situated corner portion of the diaper and that leakage will occur in this corner before the absorbent material of the diaper has been utilised to any appreciable extent.

FIGS. 6 and 7 show a suitable embodiment with which the last-mentioned lateral leakage problem has essentially been eliminated. Only those parts of the absorbent article which are essential to the demonstration of the function are shown on the drawing. Other parts, such as the outer cover, elastic, fastening arrangements, etc. have been omitted to facilitate comprehension. In the diaper in FIG. 6, intermediate storage areas 13, 14, 15 and 16 are arranged one at each side edge portion of the front and rear portions 17 and 18 of the diaper. The crotch portion of the diaper is denoted by the numeral 19. As in the embodiment shown above, the embodiment in FIG. 6 comprises liquid storage regions 2, 3 and a liquid acquisition region situated directly in front of the wetting point. A wicking layer 20 extends under the liquid storage regions 2 and 3 and under the liquid acquisition region 1 and further extends laterally out under the intermediate storage regions 14 and 16 in the front and rear portions 17 and 18 on the first side edge portion of the article. A second wicking layer 21, formed in one piece, is arranged on the upper side of the liquid storage regions 2 and 3 and extends laterally out to and under the intermediate storage regions 13 and 15 on the second side edge portion of the article.

The term 'upper side' denotes the side of, for example, the storage regions which is closest to the user during use of the article. The term 'under' which is used is defined in a similar way, i.e. 'under' has been used as the reverse of the upper side.

The second wicking layer 21 has an opening 22 directly in front of the liquid acquisition region so that liquid emitted by the user can gain access to the liquid acquisition region 1 without the wicking layer 21 being an obstacle to the collection of liquid emitted by the user.

The intermediate storage regions 13, 14, 15 and 16 are intended to be able to quickly absorb liquid which has initially accumulated in the edge portions of the diaper, so that the risk of lateral leakage when the user is lying down on his/her side is considerably reduced in relation to previously known diapers and the like.

The arrangement of liquid-impermeable portions between parts of overlapping portions of dispersion and storage layers in order to render more effective the dispersion of liquid in the longitudinal direction of the article against the force of gravity and thereby achieve a better utilisation of absorbent material in the article has been described in the embodiments in FIGS. 1–5.

In the embodiment in accordance with FIG. 6, liquid-impermeable portions 23, 24, 25 and 26 have been arranged in order to promote liquid dispersion against the force of gravity in a direction from the intermediate storage regions to the storage regions 2 and 3. The liquid-impermeable portion 23 extends in the longitudinal direction of the article over in substance the entire storage region and overlaps a side edge portion of the liquid storage region 2 nearest the second side edge portion of the article and extends further between adjacent parts of the wicking layer 21 and the side edge of the liquid storage region 2 and further a distance out under only the wicking layer 21 in a direction towards a proximate intermediate storage region 13. As can been seen in FIG. 6, the liquid-impermeable portion 25 is arranged in a corresponding manner in the rear portion of the article. The liquid-impermeable portion 24 extends in the longitudinal direction of the article over in principal the entire liquid storage layer 2 and overlaps a side edge portion of the liquid storage region 2 nearest the first side edge portion of the article and extends further between adjacent parts of the wicking layer and the side edge of the liquid storage layer and further a distance out over only the wicking layer 20. The liquid-impermeable portion 26 in the rear portion 18 of the article is arranged in a corresponding manner to the liquid-impermeable portion 24.

The function of the liquid-impermeable portions is described below with reference to FIG. 7. This figure illustrates schematically the condition of the diaper when the user is lying on his/her side and the intermediate storage region 14 constitutes the lowest part of the diaper. In an initial stage, liquid emitted by the user runs down in the edge portion and accumulates in the intermediate storage region 14. This, like the other intermediate storage regions, is formed of a material which has the ability to quickly absorb large quantities of liquid. The intermediate storage regions may possibly have a somewhat greater ability to retain liquid than the liquid acquisition area 1 since the risk of leakage is greater when liquid accumulates in the side edge of the article than in the crotch area if no measures have been taken to liquid-impermeably enclose the intermediate storage regions. However, if the intermediate storage regions are arranged in liquid-impermeable pockets, it is suitable that the liquid affinity is lower in the intermediate storage areas than in the liquid acquisition area, as in such a case liquid can be lifted up from the intermediate storage areas also to the liquid acquisition area 1 when the user is lying on his/her side, whereby the risk of edge leakage due to over-saturation of the intermediate storage areas is reduced.

In a corresponding way to that described in connection with FIG. 1, liquid is dispersed from the lowest situated initial accumulation place against the force of gravity to the storage region 2. Liquid which, as is shown in FIG. 7, is dispersed in the direction of the arrow A in the wicking layer 20 is prevented by the liquid-impermeable layer 24 from being transferred to the storage region 2. Only when the liquid has been lifted up over the upper end edge 24' can the liquid be dispersed in the storage region. In the storage region 2 the liquid is dispersed equally in all directions, disregarding the effect of gravity. When the user is lying on his/her side, gravity naturally has an effect and liquid that has passed the edge 24' would have a tendency to spread more downwards than upwards if the wicking layer had not extended beyond the edge 24'. The wicking layer can, however, be formed so that it more than amply compensates for said tendency, i.e. so that liquid is able to be filled last into the lowest situated parts of the storage region.

As is mentioned above in the description relating to FIG. 1, the length of the liquid-impermeable portions 23, 24, 25 and 26 and the design of the wicking layers can be chosen depending on the absorption and dispersion characteristics of the materials in the article for optimal utilisation of the absorption-material in the storage regions 2, 3.

In the embodiment in FIGS. 6 and 7 the wicking layers 20 and 21 are situated on opposite sides of the storage regions. Furthermore, the liquid-impermeable portions 23, 24 and 25, 26, respectively, are situated with their active parts on opposite sides of the storage areas, which can be seen most clearly in FIG. 6. However, with regard to dispersion and absorption properties, the article is symmetrical, i.e. liquid is absorbed equally effectively from the intermediate storage area 13 as from the intermediate storage region 14.

The embodiment shown in FIG. 6 is schematic with regard to the form and extension of the constituent parts. For example, the form of the intermediate storage regions can be different and the size in relation to the storage regions can also be other than what is shown. The size and form of the intermediate storage regions 13, 14, 15 and 16 and the storage regions 2, 3 naturally depends on the choice of materials included and on how the article as a whole is formed.

The embodiment in FIG. 8 differs from the embodiment in FIGS. 6 and 7 only in that additional wicking layers 27, 28 have been arranged on either side of the respective liquid storage region 2, 3 and that the liquid-impermeable portions 23, 24, 25 and 26 have been arranged between the wicking layers, as can be seen in FIG. 8, and also in that the liquid-impermeable portions extend a longer distance in the transverse direction over the liquid storage region. This can be suitable depending on material included and/or whether the transport distances are long. The additional wicking layers 27, 28 can thus, under certain circumstances, facilitate the dispersion in the storage area under the liquid-impermeable portion 23 so that the material in the lowest situated part of the storage region is also used.

During use of the absorbent article in accordance with the embodiments shown in FIGS. 6, 7 and 8 it is important that liquid that has accumulated initially in one or several intermediate storage regions on one side of the diaper can quickly be transported to a proximate liquid storage region so that on the next wetting, the intermediate storage regions will have regained in principal all of their original capacity to quickly absorb large quantities of liquid. The choice of material in the storage region, wicking layers and intermediate storage regions is not critical. What is essential is that the suction power of the storage region exceeds the sum of the retention capacity in the intermediate storage regions and the necessary suction height. Types of material which can be used in the intermediate storage regions 13, 14, 15 and 16 are fibre structures, foam or similar porous materials. For example, it is possible to use HT-CTMP, which is a cellulose fluff pulp with low wettability.

By ensuring that the constituent parts of the article, the liquid storage regions 2, 3, the liquid acquisition region 1, the intermediate storage regions 13, 14, 15 and 16 and the wicking layers 20, 21, display differences in wetting angles, it is possible to obtain a controlled and predictable liquid dispersion from the intermediate storage regions to the liquid storage regions and from the liquid acquisition region 1 to the liquid storage regions.

A material or a combination of materials which give good liquid dispersion ability is of course chosen as the material in the liquid dispersion regions. One material that can be used is chemically produced cellulose fluff pulp (CP) with a surface weight of ca 200 g/m$^2$.

Another example of suitable material is the absorbent material described in WO 94/10956. This material is a dry-formed fibre layer which is used directly in an absorbent article without previous defibration.

The material used in the liquid storage areas 2, 3 should have high wettability and high capillary pressure. As mentioned above, mixtures of fluff pulp and high absorbent material, usually called superabsorbents, are suitable materials.

As mentioned above, a cellulose fluff pulp with low wettability, for example, is suitable for use in the intermediate storage regions.

The international application PCT/SE98/00078 describes absorbent material in the form of chemithermomechanical cellulose fluff pulp (CTMP) in which the surface of the CTMP fibres has been treated with an agent to increase the receding wetting angle from 0–10 degrees to ca. 40 degrees, which means that even after wetting, the absorbent structure has relatively low wettability.

Other types of absorbent material can also be treated in order to reduce the change in wettability which otherwise arises on wetting.

The term dynamic contact angle refers to the angle which is shown when a liquid front moves. The terms advancing wetting angle and receding wetting angle are intended to indicate whether the dynamic contact angle is measured when a liquid advances over a dry surface or if the liquid retreats over a newly wetted surface.

A material which can be used to increase the receding wetting angle is ethylhydroxyethyl cellulose (EHEC).

In the embodiment in FIGS. 9–11, those parts which correspond to similar parts in FIGS. 6–8 have been given the same reference numerals. The cross section in FIG. 10 is completely identical to FIG. 8, which means that additional wicking layers 27 and 28 are arranged on either side of the storage regions 2, 3. In the embodiment in FIGS. 9–11, unlike the embodiments in FIGS. 6–8, liquid-impermeable portions are arranged in the longitudinal direction in order to effectively disperse to the liquid storage regions 2, 3 liquid which has initially accumulated in the liquid acquisition region 1. The liquid-impermeable layers, which promote liquid dispersion in the longitudinal direction of the article; have the same function as the portions described in the embodiments in FIGS. 1 and 2 and have been given the same reference numbers 5, 6. As can be seen in FIG. 11, the liquid-impermeable portion 6 delimits the end of the liquid storage region 3 from the end of the liquid acquisition region 1. Furthermore, it extends a distance between the liquid storage layer 3 and the additional wicking layer 28 in order to prevent the transfer of liquid from the wicking layer to the storage area until the end edge 6' of the liquid-impermeable portion has been passed.

In the embodiment in FIGS. 9–11, dispersion of liquid in the article against the force of gravity is promoted both from initial accumulation places in the crotch portion and from initial accumulation places 13–16 in the edge portions of the article by means of liquid-impermeable portions which are arranged over parts of overlapping parts of wicking layers and liquid storage areas.

As can be seen in FIG. 11, the liquid-impermeable portion 6 has been arranged over the wicking layer 28 while the liquid-impermeable layer 26 is arranged under said wicking layer. By means of this arrangement, the liquid-impermeable layers 6 and 26 could overlap one another without liquid dispersion in the longitudinal direction being disrupted by the liquid-impermeable portions arranged to promote liquid dispersion laterally since liquid dispersion can take place in the wicking layer 28 between the two liquid-impermeable portions 6 and 25.

The embodiment in FIGS. 12 and 13 comprises a wicking layer 29 formed in one single piece. In FIGS. 12 and 13 the parts which correspond to similar parts in the above-described embodiment example have been given the same reference numerals.

In this embodiment, the liquid-impermeable portions 23, 24 and 25, 26 are located on the same side of the liquid storage regions 2, 3. To enable liquid dispersion to occur effectively in the vertical direction from, for example the intermediate storage region 13 to the most distant parts of the storage region in the lateral direction (the vertical direction in FIG. 13) of the article, a further wicking layer 30 has been arranged between the liquid-impermeable portions 23, 24 and the storage region 2 and between the liquid-impermeable portions 25, 26 and the storage region 3.

The embodiment example in FIGS. 14 and 15 differs from the embodiment shown in FIGS. 12 and 13 only in that liquid-impermeable portions 5 and 6 have been arranged in order to improve the dispersion in the longitudinal direction of the article from the liquid acquisition region 1 in the crotch portion of the article to the two storage regions. Accordingly, the liquid-impermeable portions 5 and 6 fulfil the same function as the liquid-impermeable portions 5, 6 described above in connection with FIGS. 1 and 2 and FIG. 11. As can be seen in FIG. 15, the liquid-impermeable portion 6 is arranged so that it delimits the end portion of the liquid acquisition region 1 from the proximate end portion of the liquid storage region 3. Moreover, the liquid-impermeable portion extends between the liquid storage region 3 and the additional wicking layer 30. It is important that the liquid-impermeable layers 5 and 6, which promote dispersion in the longitudinal direction, lie in a different plane from the liquid-impermeable portions 23, 24; 25 and 26, which promote dispersion in the lateral direction. If they lay in the same plane, the flow in the longitudinal direction would be disrupted by the liquid-impermeable portions 23, 24, 25 and 26 and vice versa. When the liquid-impermeable portions are arranged in different planes they can even overlap one another in the longitudinal direction if this were desirable in order to optimise the dispersion with regard to the materials included.

Examples of suitable materials for the liquid storage regions, wicking layers, intermediate storage regions and liquid acquisition region have been given above.

The material in the liquid-impermeable portions can be, for example, a plastic film, such as polyethylene or polyester.

Another example of suitable material for the liquid-impermeable portions is nonwoven treated with hydrophobising agent. This can be suitable if it is desirable that the absorbent article be permeable to air and one does not wish to disrupt this function with airtight portions.

In absorbent articles which comprise fluff pulp of cellulose, the fluff pulp is often strengthened by binding adjacent layers with the fluff pulp by means of a binding agent. According to a suitable embodiment, the liquid-impermeable portions consist of hydrophobic binding agent. In this way, the function of liquid impermeable portions in accordance with the invention can be achieved in principal without extra material and extra costs in comparison with earlier known absorbent articles. Also in embodiments in which the absorbent material consists of fluff pulp, it can be suitable to connect different layers and to combine liquid-impermeable portions in order to promote both liquid dispersion and increase the strength.

Absorbent artices, such as diapers, usually comprise elastic portions to obtain sealing or forming of the article. In accordance with a suitable embodiment, the liquid-impermeable portions for the promotion of liquid dispersion are also elastic, whereby the portions can also serve as elastic for forming or sealing the article. By means of, for example, forming, bowl-like areas can be created which can serve as liquid acquisition pockets, for example initial accumulation places, from which desired liquid dispersion is promoted by said liquid-impermeable and elastic portions. During manufacture of absorbent articles, such as diapers, at high speed, elastic portions which are included in the article are complicated to handle. If the liquid-impermeable portions are also to be elastic, they can suitably be formed of a plastic film of a type which shrinks and becomes elastic when heat-treated. Accordingly, plastic films of this kind are applied in unstretched condition during manufacture and are thereafter, for example when the articles are packaged, heat-treated to induce shrinkage and elastication.

The invention is not limited to the embodiments described above, a number of modifications being possible within the limits of the following claims.

In the embodiments shown above which comprise liquid-impermeable portions 5, 6 which promote dispersion in the longitudinal direction of the article, parts of said portions 5, 6 are arranged to prevent direct transfer of liquid from the liquid acquisition region to adjacent liquid storage regions. Naturally, it is possible within the limits of the invention to arrange liquid-impermeable portions 5, 6 which allow direct transfer from the liquid acquisition region 1 to the storage regions 2, 3. In such an embodiment, liquid is filled into the liquid storage regions both directly from the liquid acquisition region and via a wicking layer which connects the liquid acquisition region 1 to the liquid storage regions. An example of such an embodiment can be obtained if in the embodiment in FIG. 1 the parts of the liquid-impermeable portions 5, 6 situated between the liquid acquisition region 1 and the liquid storage regions 2, 3 are removed.

What is claimed is:

1. An absorbent article, comprising at least one liquid storage region with high absorption capacity and at least one wicking layer which overlaps at least a substantial part of the liquid storage region and which has greater liquid dispersion ability than the liquid storage region, wherein the wicking layer is intended to disperse liquid collected locally in the article over the liquid storage region, and wherein at least one liquid-impermeable portion is arranged between the wicking layer and the liquid storage region, wherein at least one initial accumulation place, in the form of a liquid acquisition region or in the form of a liquid acquisition region and intermediate storage regions, is arranged to quickly take up liquid emitted by the user, the article comprising at least one said wicking layer, said wicking layer arranged to disperse liquid collected in said initial accumulation place to said liquid storage region, liquid-impermeable portions are arranged in the article along parts of overlapping sections of the wicking layer and the liquid storage region in order to prevent the transfer of liquid over said parts from the wicking layer to the liquid storage region, said liquid impermeable portions extend a distance from the end of the liquid storage region that faces towards said initial accumulation place, whereby liquid collected in the accumulation place is first dispersed in the wicking layer along said parts separated from the liquid storage region and thereafter is dispersed further in the liquid storage region at a distance from said accumulation place.

2. An absorbent article in accordance with claim 1, wherein the article in a manner known in itself, has a front portion a rear portion and an intermediate preferably narrower crotch portion, that a liquid acquisition region with the ability to quickly absorb large amounts of liquid is arranged in the crotch portion and serves as said initial accumulation place, that liquid storage regions are arranged at least in the front portion and rear portion at each end of the liquid acquisition region, that said wicking layer comprises a wicking layer, preferably formed in one piece, which is arranged behind said liquid acquisition region seen from the side of the article that is facing towards the user during use and which overlaps at least the main part of said liquid storage regions in the forward and rear portion.

3. An absorbent article in accordance with claim 2, wherein said liquid-impermeable portions are arranged at least between the wicking layer and said liquid storage regions in the front and rear portions, wherein a first liquid-impermeable portion extends a distance from the end of the liquid storage region that faces towards the liquid acquisition region in the front portion and a second liquid-impermeable portion extends a distance from the end of the liquid storage region that faces towards the liquid acquisition region in the rear portion.

4. An absorbent article in accordance with claim 2, wherein a further wicking layer is arranged immediately behind the respective liquid storage layer in the front and rear portions and that said liquid impermeable portions are arranged at least between the two wicking layers, wherein a first liquid-impermeable portion extends a distance from the end of the liquid storage region that faces towards the liquid acquisition region in the front portion and a second liquid-impermeable portion extends a distance from the end of the liquid storage region that faces towards the liquid acquisition area in the rear portion.

5. An absorbent article in accordance with claim 3, wherein the article contains a liquid-impermeable layer which extends over the front and rear portions and the crotch portion and which, seen from the side which faces the user during use of the article, is arranged above said liquid storage regions and the liquid acquisition region, that the liquid-impermeable layer has an opening immediately in front of the liquid acquisition region, which opening suitably extends in the longitudinal direction of the article a distance which corresponds to the distance between adjacent end portions of the liquid storage regions in the front and rear portions, that said opening has been formed by making slits through the liquid-impermeable layer along the longitudinal border lines of the intended opening and a horizontal slit between said lines in the central area of the intended opening and by folding in the flaps made by the slits, and that the flaps are folded in under the liquid storage regions in the front and rear portions in order to form the liquid-impermeable portions.

6. An absorbent article in accordance with claim 2, wherein intermediate storage regions intended to collect initially accumulated liquid are arranged one on either side edge portion of the front and rear portions, that the intermediate storage regions are situated at a distance laterally from said liquid storage region and are connected to these by means of at least said wicking layer.

7. An absorbent article in accordance with claim 6, wherein said wicking layer, which is arranged behind the liquid acquisition region, extends under the liquid storage regions in the front and rear portions and out to and under the intermediate storage regions in the front and rear portions on the first of the side edge portions of the article, that a second wicking layer is arranged on the upper side and over at least the main part of the liquid storage regions in the front and rear portions and extends out to and under the intermediate storage regions in the front and rear portions on the second side edge portion of the article, that the second wicking layer has an opening immediately in front of the liquid acquisition region, and that the liquid-impermeable portions comprise a liquid-impermeable portion arranged at the respective liquid storage layer in the front and rear portions, which liquid-impermeable portion extends in the longitudinal direction of the article over at least the main part of the liquid storage layer and overlaps a side edge portion of the liquid storage layer nearest the first side edge portion of the article and extends further between adjacent parts of the wicking layer and the side edge of the liquid storage layer and suitably a distance out over only the wicking layer in a direction towards a proximate intermediate storage region, and also comprise a liquid-impermeable portion arranged at the respective liquid storage region in the front and rear portions, which liquid-impermeable portion extends in the longitudinal direction of the article over at least the main part of the liquid storage region and overlaps a side edge portion of the liquid storage region nearest the second side edge portion of the article and extends further between adjacent parts of the wicking layer and the side edge of the liquid storage region and suitably a distance out over only the wicking layer in a direction towards a proximate intermediate storage region.

8. An absorbent article in accordance with claim 7, wherein an additional wicking layer is arranged on each side surface of and in direct contact with the respective liquid storage region, and that said liquid-impermeable portions are arranged between said additional wicking layer and the first-mentioned and the second wicking layer, respectively.

9. An absorbent article in accordance with claim 6, wherein said wicking layer arranged behind the liquid acquisition region extends under the liquid storage regions in the front and rear portions and out to and under the intermediate storage regions at each side edge portion of the front and rear portions, that behind and in direct contact with the respective liquid storage region is arranged a second wicking layer, that the liquid-impermeable portions comprise liquid-impermeable portions arranged between the two wicking layers along the longitudinal side portions of the liquid storage regions in the front and rear portions, wherein each of the said liquid-impermeable portions extends in the longitudinal direction of the article over at least the main part of the liquid storage region and overlaps a side edge portion of the liquid storage region and extends further laterally outwards between adjacent parts of the first-mentioned wicking layer and the side edge of the liquid storage region and suitably a distance out over only the first-mentioned wicking layer in a direction towards a proximate intermediate storage region.

10. An absorbent article in accordance with claim 7, wherein behind at least the respective liquid storage region seen from the side which faces towards the user during use of the article a third wicking layer is arranged in direct contact against the respective liquid storage region, that further liquid-impermeable portions are arranged in the forward and rear portions either between the first-mentioned wicking layer and the third wicking layer or between the liquid storage region and the third wicking layer, wherein a first of the said further liquid-impermeable portions extends a distance from the end of the liquid storage region that faces the liquid acquisition region in the front portion and a second of the said further liquid-impermeable portions extends a distance from the end of the liquid storage region that faces the liquid acquisition region in the rear portion.

11. An absorbent article in accordance with claim 9, wherein further liquid-impermeable portions are arranged between the second wicking layer and the liquid storage region in the front and rear portions, wherein a first of the said further liquid-impermeable portions extends a distance from the end of the liquid storage region that faces the liquid acquisition region in the front portion and a second of the said further liquid-impermeable portions extends a distance from the end of the liquid storage region that faces the liquid acquisition region in the rear portion.

12. An absorbent article in accordance with claim 6, wherein the material in the liquid storage regions has greater liquid affinity than the material in the intermediate storage regions, whereby transfer of liquid from the intermediate storage regions to the liquid storage regions is promoted.

13. An absorbent article in accordance with claim 1, wherein the liquid-impermeable portions are formed of a plastic film.

14. An absorbent article in accordance with claim 1, wherein the liquid-impermeable portions are constituted of a nonwoven treated with hydrophobising agent.

15. An absorbent article in accordance with claim 1, wherein the liquid-impermeable portions are constituted of hydrophobic coatings.

16. An absorbent article in accordance with claim 1, wherein at least one of the liquid-impermeable portions is elastic in one or several directions and is also used for preforming of the absorbent article.

17. An absorbent article in accordance with claim 16, wherein the elastic liquid-impermeable portions are formed of plastic films which shrink and become elastic after heat treatment.

18. An absorbent article in accordance with claim 3, wherein the ends of the liquid storage regions which are facing towards the liquid acquisition region are covered by parts of the liquid-impermeable portions so that liquid from the liquid acquisition region in the crotch portion can only reach the liquid storage regions via the wicking layers.

19. An absorbent article in accordance with claim 1, wherein the absorbent article is a diaper or an incontinence protector.

20. An absorbent article in accordance with claim 13, wherein the plastic film is polyethylene.

21. An absorbent article in accordance with claim 15, wherein the hydrophobic coatings are a hydrophobic binding agent.

* * * * *